(12) United States Patent
Maehara

(10) Patent No.: US 7,714,153 B2
(45) Date of Patent: May 11, 2010

(54) CURABLE DIAMANTANE COMPOUND

(75) Inventor: Takayuki Maehara, Shunan (JP)

(73) Assignee: Tokuyama Corporation, Yamaguchi (JP)

( * ) Notice: Subject to any disclaimer, the term of this patent is extended or adjusted under 35 U.S.C. 154(b) by 588 days.

(21) Appl. No.: 11/664,290

(22) PCT Filed: Sep. 29, 2005

(86) PCT No.: PCT/JP2005/018218

§ 371 (c)(1),
(2), (4) Date: Apr. 23, 2007

(87) PCT Pub. No.: WO2006/035955

PCT Pub. Date: Apr. 6, 2006

(65) Prior Publication Data

US 2008/0071052 A1    Mar. 20, 2008

(30) Foreign Application Priority Data

Sep. 30, 2004    (JP) .............................. 2004-286545

(51) Int. Cl.
*C07D 303/20*    (2006.01)
*C07D 303/22*    (2006.01)
*C07D 305/06*    (2006.01)

(52) U.S. Cl. ................. 549/554; 549/510; 549/512; 549/560; 257/100

(58) Field of Classification Search ................ 549/510, 549/512, 554, 560; 257/100
See application file for complete search history.

(56) References Cited

FOREIGN PATENT DOCUMENTS

| JP | 2003-73452 A | 3/2003 |
| JP | 2005-146253 A | 6/2005 |

OTHER PUBLICATIONS

Jiri Burkhard, et al., "Diamantylmethanols: their oxidation by lead (IV) acetate", Scientific Papers of the Prague Institute of Chemical Technology, vol. 5, Jan. 1, 1984, pp. 5-23.

Frantisek Turecek, et al., "Cycloheptatriene dimers: new precursors of diamantane", Collection of Czechoslovak Chemical Communications., vol. 46, (1981), pp. 1474-1485.

*Primary Examiner*—Bernard Dentz
(74) *Attorney, Agent, or Firm*—Birch, Stewart, Kolasch & Birch, LLP

(57) ABSTRACT

A 4,9-bis(glycidyloxy)diamantane and a 4,9-bis[(3-ethyloxetane-3-yl)methyloxy]diamantane are novel curable diamantane compounds, and cured bodies thereof are useful as encapsulants exhibiting excellent light resistance and heat resistance, and can be favorably used, for example, as encapsulants for near ultraviolet LEDs and white LEDs.

4 Claims, 4 Drawing Sheets

CURABLE DIAMANTANE COMPOUND

TECHNICAL FIELD

The present invention relates to a novel and curable diamantane compound useful as a starting material for encapsulants and adhesives.

BACKGROUND ART

Light-emitting diodes (LEDs) have been vigorously developed in recent years accompanied by the development of aluminum/indium/gallium/phosphorus (AlInGaP) that emits light in red to orange colors and gallium nitride (GaN) that emits light in a blue color as light-emitting materials. There have further been realized LEDs that emit near ultraviolet rays of shorter than 400 nm, such as 365 nm and 370 nm. An LED which emits white light has also been accomplished by combining, for example, a fluorescent material with a blue LED or a near ultraviolet LED.

The LED has many advantages such as a long life, a high temperature stability, easy dimming and a low driving voltage, and has positively been applied to displays, indicator boards, car-mounted illumination, signal lamps, cell phones, video cameras and the like. In particular, a white LED has been developed for illumination purposes and has been very expected as a source of light to substitute for the conventional incandescent lamps, halogen lamps and fluorescent lamps. For its widespread use, however, it is desired to further improve the brightness and efficiency as a source of light.

In these applications, the LED is usually used being packaged. In mounting the LED on a package, in general, the LED is joined to a predetermined position in the package while electrically connecting the electrodes of the package to the electrodes of the LED, and is sealed with a transparent sealant for protecting the LED. A widely used sealant can be represented by an epoxy resin using a bisphenol A-type glycidyl ether on account of its highly adhering property, good operability and low cost.

However, the above epoxy resin sealant cannot meet the shortened wavelengths and high brightness of the LED. When used for sealing the near ultraviolet LED and white LED, therefore, there arouse such problems that the resin is deteriorated and becomes yellow causing the brightness of the LED device to decrease and the color tone to be varied.

Studies have been forwarded to solve these problems without, however, finding any solution. For example, the light resistance can be improved to some extent by adding an alicyclic epoxy compound to a hydrogenated bisphenol A type glycidyl ether. However, the degree of improvement is far from the practicable level and the heat resistance is rather lowered (e.g., see patent document 1). Further, by using a curable adamantane compound which is an epoxy compound using adamantane as a basic skeleton, there can be obtained a resin with a heat resistance higher than that of the hydrogenated bisphenol A glycidyl ether, which, however, is not still of a sufficient level (see, for example, patent document 2). When a phosphorus type antioxidant is added, discoloration due to the heat can be suppressed to some extent causing, however, the light resistance to be deteriorated.

Patent Document 1: JP-A-2003-73452
Patent Document 2: JP-A-2005-146253

DISCLOSURE OF THE INVENTION

In sealing the LEDs and, particularly, the near ultraviolet LEDs and white LEDs as described above, it is desired to improve the light resistance, heat resistance and adhesiveness of the sealing agent.

It is, therefore, an object of the present invention to provide a novel monomer (curable compound) capable of forming a cured body such as a sealant featuring excellent light resistance and heat resistance.

The present inventors have conducted keen study in an attempt to solve the above problems. As a result, the inventors have discovered that a novel and curable diamantane compound obtained by introducing an epoxy group or an oxetanyl group as a polymerizable functional group to the diamantanes, not only forms a cured body having high heat resistance and light resistance but also features a small shrinkage when cured, can be favorably used as an adhesive for optical use and for highly heat resistant use and as a sealant for semiconductor lasers, and have completed the present invention.

That is, according to the present invention, there is provided a curable diamantane compound represented by the following formula (1),

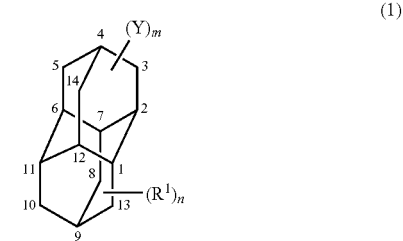

$$(1)$$

wherein m is an integer of 1 to 4, n is an integer of 0 to 4, $R^1$ is an alkyl group having 1 to 5 carbon atoms, and Y is a group represented by the following formula (2),

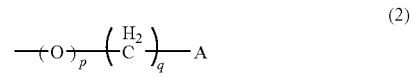

$$(2)$$

wherein p is 0 or 1, q is an integer of 0 to 6, and A is a group represented by the following formula 3(a) or 3(b),

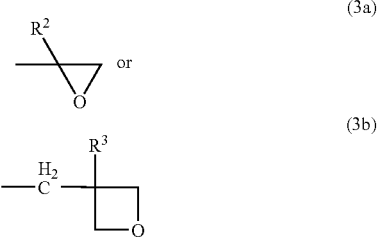

$$(3a)$$

$$(3b)$$

wherein $R^2$ is a hydrogen atom, a methyl group or an ethyl group, and $R^3$ is a methyl group or an ethyl group.

The curable diamantane compound of the present invention forms a cured body having excellent optical properties, heat resistance and light resistance, and features a small shrinkage when cured. Therefore, this compound can be particularly preferably used as a starting material for a encapsulant or sealant used for encapsulating or sealing near ultraviolet LEDs and white LEDs.

Besides, these properties are significantly higher than those of the hydrogenated bisphenol A type glycidyl ether and those of even the curable adamantane compounds. As compared to the adamantane, in general, the diamantane has many tertiary carbon moieties which are relatively and cationically stable and are highly reactive, and has a low degree of polymerization since its molecular size is greater than that of the adamantane, and is expected to be easily decomposed by heat. Astonishingly, however, the curable diamantane compound of the present invention has a higher heat resistance than that of the adamantane. Such excellent effects are obtained probably because the diamantane has a structure more rigid than the adamantane.

BEST MODE FOR CARRYING OUT THE INVENTION

Figure 1:
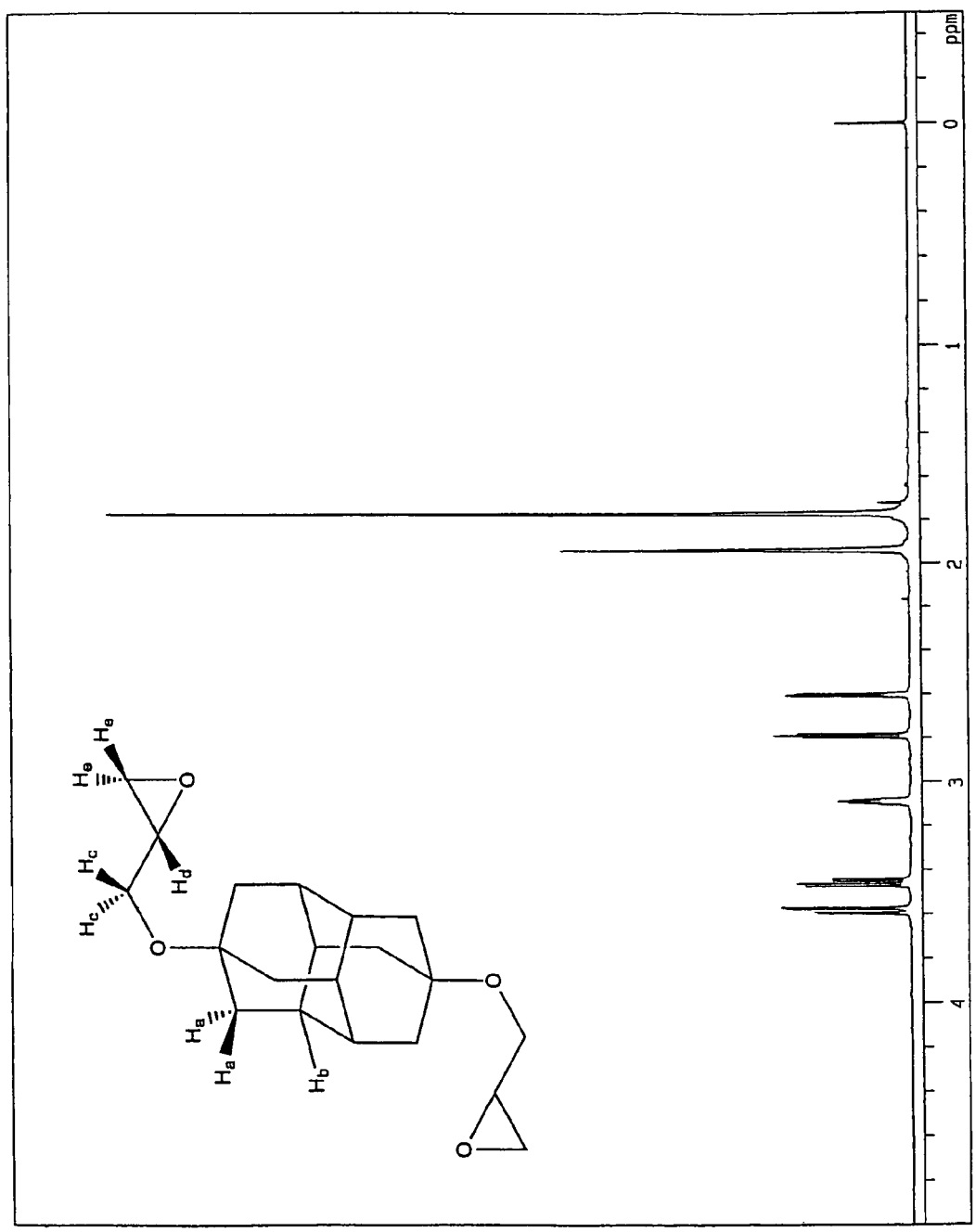
FIG. 1 shows $^1$H-NMR spectra of a 4,9-bis(glycidyloxy)diamantane obtained in Example 1.

The curable diamantane compound of the present invention is a novel compound obtained by introducing an epoxy group or an oxetanyl group as a polymerizable functional group to the diamantanes, and can be produced by using corresponding diamantanes as starting materials.

Described hereinafter in detail are the curable diamantane compound of the present invention, the reactant (starting reaction material, catalyst, etc.) used in the production method therefor, reaction conditions, procedure of reaction and products.

(Curable Diamantane Compound)

A curable diamantane compound of the present invention is expressed by the following formula (1). Numerals in the formula represent positions of carbon atoms.

$$\text{(1)}$$

In the above formula (1), m is an integer of 1 to 4. From the easiness of production, it is desired that m is an integer of 1 to 3 and, particularly, 3. Further, n is an integer of 0 to 4. From the easiness of production, it is desired that n is an integer of 0 to 2 and, particularly, 0.

In the above formula (1), $R^1$ is an alkyl group having 1 to 5 carbon atoms. As the alkyl group, there can be exemplified a methyl group, an ethyl group, an n-propyl group, an isopropyl group, an n-butyl group, a sec-butyl group, a t-butyl group, an n-pentyl group, a sec-pentyl group and an isopentyl group. Among them, the methyl group is particularly preferred.

In the above formula (1), Y is a group represented by the following formula (2), $$-\!(\text{O})_p\!-\!(\text{CH}_2)_q\!-\!A \qquad (2)$$

In the above formula (2), p is 0 or 1. Further, q is an integer of 0 to 6. From the easiness of production, it is desired that q is an integer of 0 to 2 and, particularly, 0 or 1.

In the formula (2), further, A is an epoxy group represented by the following formula (3a) or an oxetane ring-containing group represented by the following formula (3b), $$\text{(3a)}$$

$$\text{(3b)}$$

In the above formulas (3a) and (3b), $R^2$ is a hydrogen atom, a methyl group or an ethyl group, and $R^3$ is a methyl group or an ethyl group.

Among the compounds represented by the above formula (1) of the present invention, concrete examples of the preferred compounds are those described in (a) to (d) below.

(a) Curable Diamantane Compounds in which p is 1 and A is an Epoxy Group Represented by the Formula (3a):
1-Glycidyloxydiamantane,
4-Glycidyloxydiamantane,
4,9-Bis(glycidyloxy)diamantane,
1,4-Bis(glycidyloxy)diamantane,
1,6-Bis(glycidyloxy)diamantane,
1,4,6-Tris(glycidyloxy)diamantane,
1,4,9-Tris(glycidyloxy)diamantane,
1-(3,4-Epoxybutyloxy)diamantane,
4-(3,4-Epoxybutyloxy)diamantane,
4,9-Bis(3,4-epoxybutyloxy)diamantane,
1,4-Bis(3,4-epoxybutyloxy)diamantane,
1,6-Bis(3,4-epoxybutyloxy)diamantane,
1,4,6-Tris(3,4-epoxybutyloxy)diamantane,
1,4,9-Tris(3,4-epoxybutyloxy)diamantane,
1-(4,5-epoxypentyloxy)diamantane,
4-(4,5-epoxypentyloxy)diamantane,
4,9-Bis(4,5-epoxypentyloxy)diamantane,
1,4-Bis(4,5-epoxypentyloxy)diamantane,
1,6-Bis(4,5-epoxypentyloxy)diamantane,
1,4,6-Tris(4,5-epoxypentyloxy)diamantane,
1,4,9-Tris(4,5-epoxypentyloxy)diamantane, (b) Curable Diamantane Compounds in which p is 1 and A is an Oxetane Ring-Containing Group Represented by the Formula (3b):
1-[(3-Ethyloxetane-3-yl)methyloxy]diamantane,
4-[(3-Ethyloxetane-3-yl)methyloxy]diamantane,
4,9-Bis[(3-Ethyloxetane-3-yl)methyloxy]diamantane,
1,4-Bis[(3-Ethyloxetane-3-yl)methyloxy]diamantane,
1,6-Bis[(3-Ethyloxetane-3-yl)methyloxy]diamantane,
1,4,6-Tris[(3-Ethyloxetane-3-yl)methyloxy]diamantane,
1,4,9-Tris[(3-Ethyloxetane-3-yl)methyloxy]diamantane, (c) Curable Diamantane Compounds in which p is 0 and A is an Epoxy Group Represented by the Formula (3a):
1-(1,2-Epoxyethyl)diamantane,
4-(1,2-Epoxyethyl)diamantane,
4,9-Bis(1,2-epoxyethyl)diamantane,
1,4-Bis(1,2-epoxyethyl)diamantane,
1,6-Bis(1,2-epoxyethyl)diamantane,
1,4,6-Tris(1,2-epoxyethyl)diamantane,
1,4,9-Tris(1,2-epoxyethyl)diamantane,
1-(2,3-Epoxypropyl)diamantane,
4-(2,3-Epoxypropyl)diamantane,
4,9-Bis(2,3-epoxypropyl)diamantane,
1,4-Bis(2,3-epoxypropyl)diamantane,
1,6-Bis(2,3-epoxypropyl)diamantane,
1,4,6-Tris(2,3-epoxypropyl)diamantane,
1,4,9-Tris(2,3-epoxypropyl)diamantane,
1-(3,4-Epoxybutyl)diamantane,
4-(3,4-Epoxybutyl)diamantane,
4,9-Bis(3,4-epoxybutyl)diamantane,
1,4-Bis(3,4-epoxybutyl)diamantane,
1,6-Bis(3,4-epoxybutyl)diamantane,
1,4,6-Tris(3,4-epoxybutyl)diamantane,
1,4,9-Tris(3,4-epoxybutyl)diamantane.

(d) Curable Diamantane Compounds in which p is 0 and A is an Oxetane Ring-Containing Group Represented by the Formula (3b):
1-[(3-Ethyloxetane-3-yl)methyl]diamantane,
4-[(3-Ethyloxetane-3-yl)methyl]diamantane,
4,9-Bis[(3-Ethyloxetane-3-yl)methyl]diamantane,
1,4-Bis[(3-Ethyloxetane-3-yl)methyl]diamantane,
1,6-Bis[(3-Ethyloxetane-3-yl)methyl]diamantane,
1,4,6-Tris[(3-Ethyloxetane-3-yl)methyl]diamantane,
1,4,9-Tris[(3-Ethyloxetane-3-yl)methyl]diamantane,
1-[(3-Ethyloxetane-3-yl)ethyl]diamantane,
4-[(3-Ethyloxetane-3-yl)ethyl]diamantane,
4,9-Bis[(3-Ethyloxetane-3-yl)ethyl]diamantane,
1,4-Bis[(3-Ethyloxetane-3-yl)ethyl]diamantane,
1,6-Bis[(3-Ethyloxetane-3-yl)ethyl]diamantane,
1,4,6-Tris[(3-Ethyloxetane-3-yl)ethyl]diamantane,
1,4,9-Tris[(3-Ethyloxetane-3-yl)ethyl]diamantane,
1-[(3-Ethyloxetane-3-yl)propyl]diamantane,
4-[(3-Ethyloxetane-3-yl)propyl]diamantane,
4,9-Bis[(3-Ethyloxetane-3-yl)propyl]diamantane,
1,4-Bis[(3-Ethyloxetane-3-yl)propyl]diamantane,
1,6-Bis[(3-Ethyloxetane-3-yl)propyl]diamantane,
1,4,6-Tris[(3-Ethyloxetane-3-yl)propyl]diamantane,
1,4,9-Tris[(3-Ethyloxetane-3-yl)propyl]diamantane, Among the compounds represented by the above formula (1) of the present invention, the compounds represented by the following formulas (4) or (5) are particularly preferred on account of that the cured bodies thereof feature a high heat resistance and a high light resistance owing to a high degree of symmetry of the compounds and an increased number of crosslinking points:

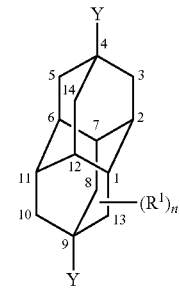

(4)

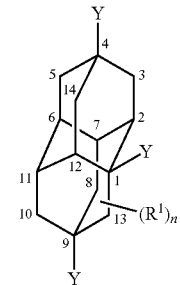

(5)

In the above formulas (4) and (5), $R^1$, n and Y are as defined in the formula (1) above.

Curable Diamantane Compounds Represented by the Formula (4):
Described below are preferred examples of the curable diamantane compound of the above formula (4).
4,9-Bis(glycidyloxy)diamantane,
4,9-Bis(3,4-epoxybutyloxy)diamantane,
4,9-Bis(4,5-epoxypentyloxy)diamantane,
4,9-Bis[(3-ethyloxetane-3-yl)methyloxy]diamantane,
4,9-Bis(1,2-epoxyethyl)diamantane,
4,9-Bis(2,3-epoxypropyl)diamantane,
4,9-Bis(3',4-epoxybutyl)diamantane,
4,9-Bis[(3-ethyloxetane-3-yl)methyl]diamantane.

Among them, the 4,9-bis(glycidyloxy)diamantane and the 4,9-bis(1,2-epoxyethyl)diamantane are particularly preferred from the standpoint of easiness of production.

Curable Diamantane Compounds Represented by the Formula (5):
Described below are preferred examples of the curable diamantane compound of the above formula (5).
1,4,9-Tris(glycidyloxy)diamantane,
1,4,9-Tris(3,4-epoxybutyl)diamantane,
1,4,9-Tris(4,5-epoxypentyloxy)diamantane,
1,4,9-Tris[(3-ethyloxetane-3-yl)methyloxy]diamantane,
1,4,9-Tris(1,2-epoxyethyl)diamantane,
1,4,9-Tris(2,3-epoxypropyl)diamantane,
1,4,9-Tris(3,4-epoxybutyl)diamantane,
1,4,9-Tris[(3-ethyloxetane-3-yl)methyl]diamantane.

Among them, the 1,4,9-tris(glycidyloxy)diamantane and the 1,4,9-tris(1,2-epoxyethyl)diamantane are particularly preferred from the standpoint of easiness of production.

(Production of Curable Diamantane Compounds)
Though there is no particular limitation on the method of producing the curable diamantane compounds of the invention, the curable diamantane compounds of (a) to (d) described above can be preferably produced by the methods described below.

Curable Diamantane Compounds (a):

The above curable diamantane compound (a)(p=1, A=epoxy group of the formula (3a)) is produced by preparing a diamantane alcoholate according to the following step (I) and, then, oxidizing the vinyl moiety of the obtained diamantane alcoholate with an oxidizing agent according to the following step (II).

Step (I):

In this step, a diamantane alcohol represented by the following formula (6) and a halogenated aralkyl represented by the following formula (7) are reacted in the presence of a base to obtain a diamantane alcoholate represented by the following formula (8).

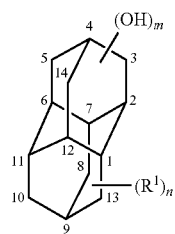
(6)

In the formula (6), m, n and $R^1$ are as defined in the formula (1) above.

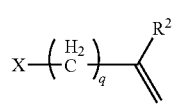
(7)

In the formula (7), X is fluorine, chlorine, bromine or iodine, and q and $R^2$ are as defined in the formula (2) above.

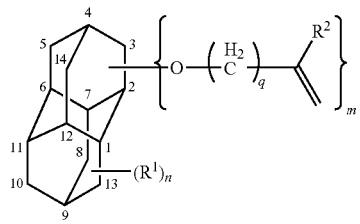
(8)

In the formula (8), $R^1$ is as defined in the formula (1) above, $R^2$ is as defined in the formula (2) above, m is an integer of 1 to 4, n is an integer of 0 to 4, and q is an integer of 0 to 6.

As the diamantane alcohols represented by the formula (6), there can be exemplified the following alcohols.

1-Diamantanol,
4-Methyl-1-diamantanol,
4-Diamantanol,
1-Methyl-4-diamantanol,
4,9-Diamantanediol,
1-Methyl-4,9-diamantanediol,
1,6-Dimethyl-4,9-diamantanediol,
1,4-Diamantanediol,
6-Methyl-1,4-diamantanediol,
9-Methyl-1,4-diamantanediol,
6,9-Dimethyl-1,4-diamantanediol,
1,6-Diamantanediol,
4-Methyl-1,6-diamantanediol,
4,9-Dimethyl-1,6-diamantanediol,
1,4,6-Diamantanetriol,
1,4,9-Diamantanetriol.

Among them, it is preferred to use the 4,9-diamantanediol or the 1,4,9-diamantanetriol and, particularly, to use the 1,4,9-diamantanetriol from the utility of the curable diamantane compound that is obtained.

As the halogenated aralkyl represented by the formula (7), there can be exemplified allyl chloride, allyl bromide, allyl iodide, 3-chloro-1-propene, 3-bromo-1-propene, 3-iodo-1-propene, 4-chloro-1-butene, 4-bromo-1-butene, 4-iodo-1-butene, 5-chloro-1-pentene, 5-bromo-1-pentene and 5-iodo-1-pentene. Among them, it is desired to use the allyl chloride, the allyl bromide or the allyl iodide from the standpoint of high degree of reactivity.

When the diamantane alcohol which is the starting material is a monoalcohol, it is desired that the halogenated aralkyl is used in an amount of 1 to 10 mol times and, particularly, 1 to 5 mol times per mol of the starting diamantane alcohol from the standpoint of accomplishing a high conversion. Further, when the starting diamantane alcohol is a dialcohol, it is desired that the halogenated aralkyl is used in an amount of 2 to 20 mol times and, particularly, 2 to 10 mol times per mol of the starting diamantane alcohol. Further, when the starting diamantane alcohol is a trialcohol, it is desired that the halogenated aralkyl is used in an amount of 3 to 30 mol times and, particularly, 3 to 15 mol times per mol of the starting diamantane alcohol.

As the base used for the reaction of the diamantane alcohol with the halogenated aralkyl, there can be used alkali metals such as lithium, sodium and potassium; alkaline earth metals such as magnesium and calcium; alkali metal hydrides such as sodium hydride and potassium hydride; alkali metal hydroxides such as lithium hydroxide, sodium hydroxide and potassium hydroxide; organic lithium compounds such as methyllithium, n-butyllithium, t-butyllithium and phenyllithium; and alkali metal alkoxides such as sodium methoxide, sodium ethoxide and potassium t-butoxide. Among them, it is desired to use sodium hydride, potassium hydride, sodium hydroxide, potassium hydroxide, or potassium t-butoxide and, particularly, sodium hydride from the standpoint of easy availability.

When the diamantane alcohol which is the starting material is a monoalcohol, it is desired that the base is used in an amount of 1 to 10 mol times and, particularly, 1 to 5 mol times per mol of the starting diamantane alcohol from the standpoint of accomplishing a high conversion. Further, when the starting diamantane alcohol is a dialcohol, it is desired that the base is used in an amount of 2 to 20 mol times and, particularly, 2 to 10 mol times per mol of the starting diamantane alcohol. Further, when the starting diamantane alcohol is a trialcohol, it is desired that the base is used in an amount of 3 to 30 mol times and, particularly, 3 to 15 mol times per mol of the starting diamantane alcohol.

It is desired that the reaction of the diamantane alcohol with the halogenated aralkyl is conducted in the presence of an organic solvent. Any known organic solvent can be used without limitation. From the standpoint of easy availability, however, it is desired to use aromatic hydrocarbons such as benzene, toluene and xylene; ethers such as diethyl ether, diisopropyl ether, di-n-butyl ether, tetrahydrofuran and dioxane; and nonprotonic polar solvents such as N,N-dimethylformamide, N,N-dimethylacetamide, dimethylsulfoxide, triamide hexamethylphosphate and N-methylpyrrolidone. Among them, it is desired to use the N,N-dimethylformamide or the tetrahydrofurane from the standpoint of a high degree of reactivity. Though there is no particular limitation on the amount of use of the organic solvent, it is desired that the organic solvent is used in an amount of 1 to 500 mol times and, particularly, 1 to 300 mol times per mol of the diamantane alcohol that is used from the standpoint of easy after-treatment.

In this case, the reaction is preferably conducted in a solvent by mixing the reaction reagents. Though there is no particular limitation on the reaction temperature, a sufficient degree of conversion is obtained, usually, at 0 to 150° C. There is no particular limitation on the reaction time, either, and a sufficient degree of conversion is obtained, usually, in 1 to 48 hours.

Step (II):

In the step (II), a vinyl moiety of the diamantane alcoholate of the formula (8) obtained through the above step (I) is oxidized with an oxidizing agent thereby to obtain a desired curable diamantane compound (a).

The oxidizing agent used in the step (II) will be peroxides such as hydrogen peroxide, peracetic acid, perbenzoic acid, m-chloroperbenzoic acid and dimethyldioxilane, or oxygen or chromic acid. Among them, it is desired to use a peroxide from the standpoint of good operability and high degree of reactivity. Among the peroxides, it is particularly desired to use m-chloroperbenzoic acid.

When there is only one vinyl moiety in the diamantane alcoholate that is to be oxidized, it is desired to use the oxidizing agent in an amount of 1 to 10 mols and, particularly, 1 to 5 mols per mol of the diamantane alcoholate. When there are two vinyl moieties in the diamantane alcoholate, it is desired to use the oxidizing agent in an amount of 2 to 20 mols and, particularly, 2 to 10 mols per mol of the diamantane alcoholate. When there are three vinyl moieties in the diamantane alcoholate, it is desired to use the oxidizing agent in an amount of 3 to 30 mols and, particularly, 3 to 15 mols per mol of the diamantane alcoholate.

It is desired that the oxidizing reaction by using the above oxidizing agent is carried out in the presence of an organic solvent. Any known organic solvent can be used without limitation. From the standpoint of easy availability, however, it is desired to use halogenated hydrocarbons such as dichloromethane, chloroform and carbon tetrachloride; aliphatic hydrocarbons such as hexane, heptane and cyclohexane; or aromatic hydrocarbons such as toluene and xylene. Among them, it is desired to use halogenated hydrocarbons such as dichloromethane, chloroform and carbon tetrachloride and, particularly, to use the dichloromethane from the standpoint of high reactivity. Though there is no particular limitation on the amount of use of the organic solvent, it is desired to use the organic solvent in an amount of 1 to 500 mole times and, particularly, 1 to 300 mol times per mole of the diamantane alcohol that is used from the standpoint of easywork-up.

The reaction is preferably conducted in a solvent by mixing the reaction reagents. Though there is no particular limitation on the reaction temperature, a sufficient degree of conversion is obtained, usually, at −20 to 100° C. There is no particular limitation on the reaction time, either, and a sufficient degree of conversion is obtained, usually, in 1 to 100 hours.

Curable Diamantane Compounds (b) and (d):

The curable diamantane compound (b) (p=1, A=oxetane ring-containing group of the formula (3b)) and the curable diamantane compound (d) (p=0, A=oxetane ring-containing group of the formula (3b)) can be produced by using an oxetane compound having a leaving group. To produce the curable diamantane compound (b) (p=1, A=oxetane ring-containing group of the formula (3b)), the diamantane alcohol of the above formula (6) may be reacted with the oxetane compound having the leaving group. To produce the curable diamantane compound (d)(p=0, A=oxetane ring-containing group of the formula (3b)), further, a Grignard compound such as 4,9-diamantanedimagnesium chloride may be reacted with the oxetane compound having a leaving group. In this case, the oxetane compound having the leaving group may be, for example, a p-toluenesulfonic ester of 3-alkyl-3-hydroxymethyloxetane (see Spanish Patent No. 2073995).

Curable Diamantane Compounds (c):

By making a reference to the method of synthesizing adamantane compounds having similar structures, the curable diamantane compound (c) (p=0, A=epoxy group of the formula (3a)) can be produced as described below.

First, a 4,9-diamantanediol is reacted with 96% sulfuric acid and 98% formic acid to prepare a 4,9-diamantanedicarboxylic acid (for example, see Collection of Czechoslovak Chemical Communications, 1983, Vol. 48, p. 1162). Next, the obtained 4,9-diamantanedicarboxylic acid is reduced with a lithium aluminum hydride to prepare a 4,9-bis(hydroxymethyl)diamantane (for example, see Chemische Berichte, 1991, Vol. 124, p. 915). Thereafter, the obtained 4,9-bis(hydroxymethyl)diamantane is reacted with a thionyl chloride to obtain a 4,9-bis(chloromethyl)diamantane followed by the Wittig reaction by using triphenylphosphine, formalin and sodium hydroxide thereby to obtain a 4,9-divinyldiamantane. The vinyl group of the obtained 4,9-divinyldiamantane is, then, oxidized to obtain a 4,9-bis(1,2,-epoxyethyl)diamantane which is the curable diamantane compound (c). It is, further, allowable to use the following general method. For example, the 4,9-diamantanecarboxylic acid is reacted with a methyllithium to obtain a 4,9-diacetyldiamantane. Then, the ketone is reduced to an alcohol with a sodium borohydride to turn the 4,9-diacetyldiamantane into a 4,9-bis(1-hydroxyethyl)diamantane which is, then, put to the dehydration reaction with a phosphoric acid aqueous solution to obtain a 4,9-divinyldiamantane. Thereafter, the vinyl group is oxidized as described above to obtain a 4,9-bis(1,2-epoxyethyl) diamantane which is the curable diamantane compound (c).

Therefore, to produce the curable diamantane compounds (c) other than those described above, the reaction should be carried in the same manner as described above by using a diamantane alcohol that corresponds to the structure thereof.

The structure of the curable diamantane compound of the present invention obtained as described above can be confirmed relying upon the $^1$H-NMR spectra and so on. In particular, the curable diamantane compound represented by the above formula (4) has an epoxy group or an oxetane ring-containing group (hereinafter often referred to simply as oxetanyl group) at 4-, 9-positions of the diamantane skeleton, exhibiting two peaks due to secondary carbon and tertiary carbon stemming from the diamantane skeleton, from which it is learned that the structure thereof is highly symmetrical.

(Properties and Use of the Curable Diamantane Compounds)

The curable diamantane compound of the present invention has a diamantane skeleton and, hence, not only forms a cured body having excellent optical properties and heat resistance but also features a small shrinkage upon polymerization since the epoxy group or the oxetanyl group has been introduced into the diamantane skeleton.

By utilizing the above properties obtained upon the homopolymerization, the curable diamantane compound of the present invention can be preferably used as a starting material for various plastic substrates, as a starting material for coating agents, as a starting material for adhesives and as a material for encapsulants. When used for the above applications, the curable diamantane compound of the present invention can also be used in combination with any other curable compounds (hereinafter referred to as coreaction agents) that are capable of reacting therewith.

There is no particular limitation on the coreaction agents provided they are capable of reacting with the curable diamantane compound of the invention, and any one that exhibits required properties depending upon the use may be selectively used. Examples of the coreaction agent that can be used for the above object include oxetane compounds, epoxy compounds and cationically polymerizable monomers. Concrete examples of the compounds that can be favorably used are as follows:

Oxetane compounds such as xylylenedioxetane, 3-ethyl-3-hydroxymethyloxetane and 3-ethyl-3-phenoxymethyloxetane;

Bisphenol A-type epoxy compounds such as bisphenol A diglycidyl ether and hydrogenated bisphenol A glycidyl ether;

Bisphenol F-type epoxy compounds such as bisphenol F diglycidyl ether;

Alicyclic epoxy compounds having a cyclohexane ring such as 3,4-epoxycyclohexylmethyl 3,4-epoxycyclohexane carboxylate;

Epoxy compounds having an isocyanuric acid skeleton such as triglycidyl isocyanurate;

Epoxy compounds such as phenol novolak type epoxy compound, glycidylamine type epoxy compound, naphthalene type epoxy compound and silicone epoxy compound;

cationically polymerizable monomers such as isobutylvinyl ether, N-vinylcarbazole, p-methoxystyrene and isobutene; and Adamantane type epoxy monomers such as 1,3-bis(glycidyloxy)adamantane, and 1,3,5-tris(glycidyloxy)adamantane.

These coreaction agents can be used in one kind or being mixed in two or more kinds.

The compositions of the curable compositions may be suitably determined depending upon the object.

From the standpoint of improving the properties by the use of the curable diamantane compound of the invention, however, it is desired that the curable diamantane compound of the invention is used in an amount in a range of 5 to 100% by mass (the remainder is the coreaction agent) on the basis of the total weight of the curable compounds.

There is no particular limitation on the method of obtaining the cured body by curing the curable diamantane compound of the invention or by curing a mixture thereof with the coreaction agent, and any known method can be employed. In effecting the curing, there can be, as required, used various additives such as filler, coupling agent, flame-retarding agent, ultraviolet ray absorber, infrared ray absorber, ultraviolet ray stabilizer, antioxidant, coloring-preventing agent, antistatic agent, dye, pigment, perfume, as well as a stabilizer.

The curable diamantane compound of the invention expressed by the formula (1) can be cured through the cationic polymerization. As the cationic polymerization initiator, there can be used the one that is, usually, used for curing the compounds having epoxy group and oxetanyl group without any particular limitation. There can be exemplified the following cationically polymerizable initiators.

Proton acids such as trifluoroacetic acid, trifluoromethanesulfonic acid and chlorosulfonic acid, and Lewis acids such as boron trifluoride, tin tetrachloride, iron chloride, phosphorus pentafluoride, arsenic pentafluoride and antimony pentafluoride;

Cationic producing materials such as iodine;

Diaryl iodonium salts such as diphenyliodonium hexafluorophosphate;

Triaryl sulfonium salts such as triphenylsulfonium hexafluorophosphate;

Phosphonium salts such as tetra-n-butylphosphonium-o,o-diethylphosphorodithioate (product name "PX-4ET", manufactured by Nihon Kagaku Kogyo Co.);

Aliphatic sulfonium salts such as 3-methyl-2-butenyltetramethylene-sulfonium hexafluoroantimonate (product name "CP-77", manufactured by Asahi Denka Co.);

Tertiary amines such as triethylamine, tributylamine, pyridine, benzyldimethylamine and 1,8-diazabicyclo[5,4,0]undeca-7-ene or organic salts thereof;

Imidazoles such as 2-methylimidazole and 2-ethyl-4-methylimidazole or organic salts thereof;

Organometal salts such as tin octylate; and

Boron trifluoride amine salt.

Among them, it is particularly desired to use phosphonium salts such as tetra-n-butylphosphonium-o,o-diethylphosphorodithioate (product name "PX-4ET", manufactured by Nihon Kagaku Kogyo Co.); aliphatic sulfonium salts such as 3-methyl-2-butenyltetramethylene-sulfonium hexafluoroantimonate (product name "CP-77", manufactured by Asahi Denka Co.); and tertiary amines such as 1,8-diazabicyclo[5,4,0]undeca-7-ene. The cationic initiator is used, desirably, in an amount of 0.01 to 10 equivalent and, particularly, 0.1 to 5 equivalent per equivalent of the epoxy group and the oxetanyl group of the curable diamantane compound of the invention.

Among the curable diamantane compounds of the invention expressed by the formula (1), the curable diamantane compound having the epoxy group can be cured by using the curing agent. As the curing agent, there can be used the one that is, usually, used for curing the epoxy compounds without any particular limitation. There can be used, for example, phenol derivatives such as bisphenol A, bisphenol F and novolak resin; acid anhydrides such as phthalic anhydride, maleic anhydride, tetrahydrophthalic anhydride, pyromellitic anhydride, 4-methylhexahydrophthalic anhydride (product name "Rikacid MH-700", manufactured by Shin-Nihon Rika Co.); amine compounds such as m-phenylenediamine, diethylenetriamine, triethylenetetramine, xylylenediamine and diaminodiphenylmethane; and polyamide. Among them, it is desired to use the acid anhydride and, particularly, the 4-methylhexahydrophthalic anhydride. The curing agent is used, preferably, in such an amount that the amount of the functional group that reacts with the epoxy group is 0.2 to 2.0 equivalents and, particularly, 0.4 to 1.8 equivalents per equivalent of the epoxy group of the curable diamantane compound. When the ratio of the functional group relative to the epoxy group is smaller than 0.4 or exceeds 1.8, the cured body that is obtained exhibits a decreased strength and decreased resistance against the water.

In effecting the curing by using a curing agent, further, the curable diamantane compound having the epoxy group can be cured by using a cure promoter. As the cure promoter, there can be used a cationic polymerization initiator described above concerning the curing through the cationic polymerization. The cure promoter is used, desirably, in an amount of 0.01 to 10% by mass and, particularly, 0.05 to 5% by mass per a mass of a mixture of the curable diamantane compound of the invention and the curing agent.

When the curable diamantane compound of the invention having the epoxy group is to be anionically polymerized by using the anionic polymerization initiator, there can be used any anionic polymerization initiator that is, usually, used for curing the epoxy compounds without any particular limitation. For example, there can be used a tertiary amine such as dibutylmethylamine or diundecylmethylamine. The anionic polymerization initiator is preferably used in such amounts that the amount of the functional group that reacts with the epoxy group is 0.01 to 10 equivalents and, particularly, 0.1 to 5 equivalents per equivalent of the epoxy group of the curable diamantane compound of the invention.

Though there is no particular limitation on the method of curing the curable diamantane compound of the invention, a curable composition containing the curable diamantane compound of the invention and the polymerization initiator or the curing agent is cured by the irradiation with light when there is used a photocationic polymerization initiator, and is cured by a treatment at room temperature or by a heat-treatment when there is used any other cationic polymerization initiator or anionic polymerization initiator.

EXAMPLES

The invention will now be described by way of Examples which, however, are not to limit the invention.

Production Example 1

A 4,9-diamantanediol (hereinafter abbreviated as 4,9-DAD) was used as a starting material.

Into a 200-ml four necked flask, there were introduced 4.4 g (0.02 mols) of the 4,9-DAD, 22 g of an N,N-dimethylformamide (in an amount 5 times as large as the 4,9-DAD on the weight basis) and 9.7 g an allyl bromide (0.08 mols, 4 mol times as great as the 4,9-DAD) in a nitrogen stream, which were heated at 30° C. and were stirred.

Next, 3.2 g (0.08 mols, 4 mol times of the 4,9-DAD) of 60% sodium hydride (oiliness) was washed with n-hexane, and was carefully added thereto so that the reaction did not undergo violently. After stirred for 9 hours, the reaction solution was analyzed with gas chromatography (hereinafter abbreviated as GC) to find that there were contained 7% of 4,9-diamantanediol, 10% of 4-allyloxy-9-diamantanol and 83% of 4,9-bis(allyloxy)diamantane in the starting material in terms of the GC purity.

Further, 50 g of a methylene chloride was added to the above reaction solution and, thereafter, the methylene chloride phase was washed six times with the ion-exchanged water in an amount of 50 g each time. Thereafter, the methylene chloride phase was condensed under reduced pressure to obtain 4.5 g of a solid material of a cream color. The obtained solid material was purified with a silica gel column chromatography (eluent: methylene chloride/ethyl acetate=10/1) to obtain 4.0 g of a white solid material {4,9-bis(allyloxy)diamantane, purity of 95%} in an yield of 63%.

Production Examples 2 to 4

The procedure was conducted in the same manner as in the Production Example 1 but using the compounds shown in Table 1 instead of the allyl bromide used in the Production Example 1. The results were as shown in Table 1.

Example 1

To 2.1 g (7 mmols) of the 4,9-bis(allyloxy)diamantane (hereinafter often referred to as starting diamantane) obtained in the Production Example 1, there were added 15 g of the methylene chloride (7 times as great as the starting diamantane on the weight basis) and 4.3 g of an m-chloroperbenzoic acid (17.4 mmols, 2.5 mole times as great as the starting diamantane), and the mixture was stirred at room temperature for 5 hours. The solution was nearly homogeneous at the start of the reaction. Accompanying the progress of the reaction, however, a solid material of m-chlorobenzoic acid has precipitated, and the reaction solution became slurry.

The GC analysis of the reaction solution indicated the contents of 2% of the 4,9-bis(allyloxy)diamantane, 86% of the 4,9-bis(glycidyloxy)diamantane and 12% of a total of unidentified by-products.

The solid material of the by-produced m-chlorobenzoic acid was separated by filtration from the reaction solution, and the filtrate was added to 15 g of a 5% sodium sulfite aqueous solution. The methylene chloride phase was washed two times with a 1N sodium hydroxide aqueous solution in an amount of 15 g each time, and was washed four times with the ion-exchanged water in an amount of 15 g each time. The methylene chloride phase was condensed under reduced pressure to obtain 1.8 g of a white solid material {containing 90% of the 4,9-bis(glycidyloxy)diamantane}.

Figure 2:
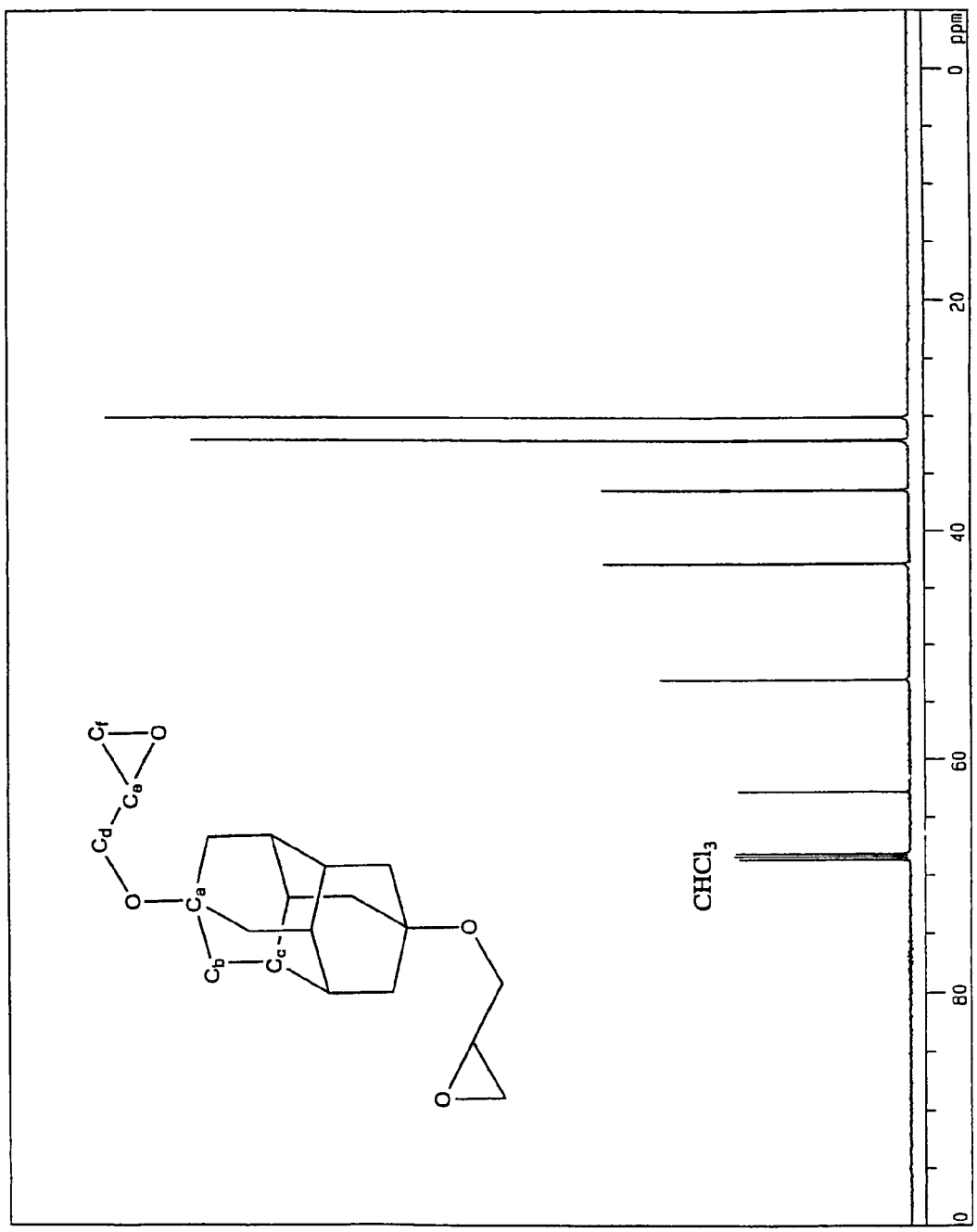
FIG. 2 shows $^{13}$C-NMR spectra of the 4,9-bis(glycidyloxy)diamantane obtained in Example 1.

To the obtained white solid material was added heptane in an amount 5 times as great on the weight basis, i.e., in an amount of 9.0 g, and the mixture was heated and stirred at 60° C. for one hour, followed by cooling down to 5° C. The obtained solid material was, then, separated by filtration to obtain 1.5 g of a white solid material {containing 98% of the 4,9-bis(glycidyloxy)diamantane} in an yield of 65%. FIG. 1 shows the $^1$H-NMR spectra of the obtained compound. FIG. 2 shows the $^{13}$C-NMR spectra of the obtained compound.

MASS (EI): molecular weight (332M$^+$)

$^1$H-NMR spectra (TMS basis): δ 1.77 ($H_a$, s, 12H), δ 1.94 ($H_b$, s, 6H), δ 2.60 to 2.80 ($H_e$, m, 4H), δ 3.01 to 3.11 ($H_d$, m, 2H), δ 3.44 to 3.60 ($H_c$, m, 4H).

$^{13}$C-NMR spectra (TMS basis): δ 30.1 ($C_c$), δ 32.1 ($C_b$) δ 36.5 ($C_f$), δ 42.8 ($C_e$), δ 653.1 ($C_d$), δ 62.8 ($C_a$).

Examples 2 to 4

The procedure was conducted in the same manner as in the Example 1 but using the compounds shown in Table 2 instead of the 4,9-bis(allyloxy)diamantane used as the starting material in the Example 1. The results were as shown in Table 2.

TABLE 1

| Production Ex. | Halogenated aralkyls | | Diamantane alcoholates | | | |
|---|---|---|---|---|---|---|
| | Compound | Amount | Compound | Obtained (g) | Yield (%) | GC purity (%) |
| 2 | 4-bromo-1-butene | 4 mol times | 4,9-bis(3,4-butenyloxy)-diamantine | 3.9 | 59 | 97 |
| 3 | 5-bromo-1-pentene | 4 mol times | 4,9-bis(4,5-pentenyloxy)-diamantine | 4.0 | 56 | 95 |
| 4 | 8-bromo-1-octene | 4 mol times | 4,9-bis(7,8-octenyloxy)-diamantane | 4.5 | 51 | 96 |

TABLE 2

| | Diamantane alcoholates | | Curable diamantane compounds | | | GC |
|---|---|---|---|---|---|---|
| Example | Compound | Amount (g) | Compound | Obtained (g) | Yield (%) | purity (%) |
| 2 | 4,9-bis(3,4-butenyloxy)-diamantine | 2.3 | 4,9-bis(3,4-epoxybutyloxy)-diamantane | 1.5 | 60 | 98 |
| 3 | 4,9-bis(4,5-pentenyloxy)-diamantine | 2.5 | 4,9-bis(4,5-epoxypentyloxy)-diamantane | 1.6 | 59 | 98 |
| 4 | 4,9-bis(7,8-octenyloxy)-diamantane | 3.1 | 4,9-bis(7,8-epoxyoctyloxy)-diamantane | 1.8 | 54 | 99 |

Production Example 5

A 1,4,9-diamantanetriol (hereinafter abbreviated as 1,4,9-DAT) was prepared as a starting material.

Into a 200-ml four neck distillation flask, there were introduced 4.7 g (0.02 mols) of the 1,4,9-DAT, 47.0 g of the N,N-dimethylformamide (in an amount 10 times as large as the 1,4,9-DAT on the weight basis) and 14.6 g of the allyl bromide (0.12 mols, 6 mol times as great as the 1,4,9-DAT) in a nitrogen stream, which were heated at 30° C. and were stirred.

Next, 4.8 g (0.12 mols, 6 mol times of the 1,4,9-DAT) of 60% sodium hydride (oiliness) was washed with n-hexane, and was carefully added thereto so that the reaction did not undergo violently. After stirred for 20 hours, the reaction solution was analyzed with GC to find that there were contained 10% of 1,4,9-DAT, 10% of monoallyloxy derivative, 25% of bisallyloxy derivative and 65% of trisallyloxy derivative in the starting material in terms of the GC purity.

Further, 100 g of the methylene chloride was added to the above reaction solution and, thereafter, the methylene chloride phase was washed six times with the ion-exchanged water in an amount of 100 g each time. Thereafter, the methylene chloride phase was condensed under reduced pressure to obtain 5.0 g of a yellow liquid.

The obtained liquid was purified with a silica gel column chromatography (eluent: methylene chloride/ethyl acetate=10/1) to obtain 4.0 g of a colorless liquid {1,4,9-tris(allyloxy)diamantane, purity of 95%} in an yield of 53%.

Production Example 6

A 1,4,9-diamantanetriol (hereinafter abbreviated as 1,4,9-DAT) was used as a starting material.

Into a 500-ml four necked flask, there were introduced 13.7 g (0.058 mols) of the 1,4,9-DAT, 68.5 g of the N,N-dimethylformamide (in an amount 5 times as large as the 1,4,9-DAT on the weight basis) and 38.6 g the allyl bromide (0.319 mols, 5.5 mol times as great as the 1,4,9-DAT) in a nitrogen stream, which were stirred at room temperature.

Next, 11.59 g (0.290 mols, 6 mol times of the 1,4,9-DAT) of 60% sodium hydride (oiliness) was washed with n-hexane, and was carefully added thereto so that the reaction did not undergo violently. After stirred for 2 hours, 7.02 g of the allyl bromide (0.058 mols, 1 mole time of the 1,4,9-DAT) was added. Next, 2.32 g (0.058 mols, 1 mol time of the 1,4,9-DAT) of 60% sodium hydride (oiliness) was washed with n-hexane, and was carefully added thereto so that the reaction did not undergo violently. After stirred at room temperature for another 4 hours, the reaction solution was analyzed with GC to find that there were contained 1% of 1,4,9-DAT, 2% of monoallyloxy derivative, 2% of bisallyloxy derivative, 85% of trisallyloxy derivative and 10% of a total of unidentified by-products in the starting material in terms of the GC purity.

To the above reaction solution were, further, added 45 g of the ion-exchanged water and 110 g of the methylene chloride, followed by the separating operation. Thereafter, the methylene chloride phase washed six times with the ion-exchanged water in an amount of 45 g each time. Thereafter, the methylene chloride phase was condensed under reduced pressure to obtain 16.3 g of an orange liquid.

The obtained liquid was purified with a silica gel column chromatography (eluent: methylene chloride/ethyl acetate=9/1) to obtain 11.2 g of a transparent liquid {1,4,9-tris(allyloxy)diamantane, purity of 90%} in an yield of 43%.

Example 5

To 8.3 g (23.2 mmols) of the 1,4,9-tris(allyloxy)diamantane (hereinafter often referred to as starting diamantane) obtained in the Production Example 6, there were added 83 g of a methylene chloride (10 times as great as the starting diamantane on the weight basis) and 18.6 g of an m-chloroperbenzoic acid (74.5 mmols, 3.2 mole times as great as the starting diamantane), and the mixture was stirred at room temperature for 12 hours. The solution was nearly homogeneous at the start of the reaction. Accompanying the progress of the reaction, however, a solid material of m-chlorobenzoic acid has precipitated, and the reaction solution became slurry.

The GC analysis of the reaction solution indicated the contents of 0% of the 1,4,9-tris(allyloxy)diamantane, 93% of the 1,4,9-tris(glycidyloxy)diamantane and 7% of a total of unidentified by-products.

Figure 3:
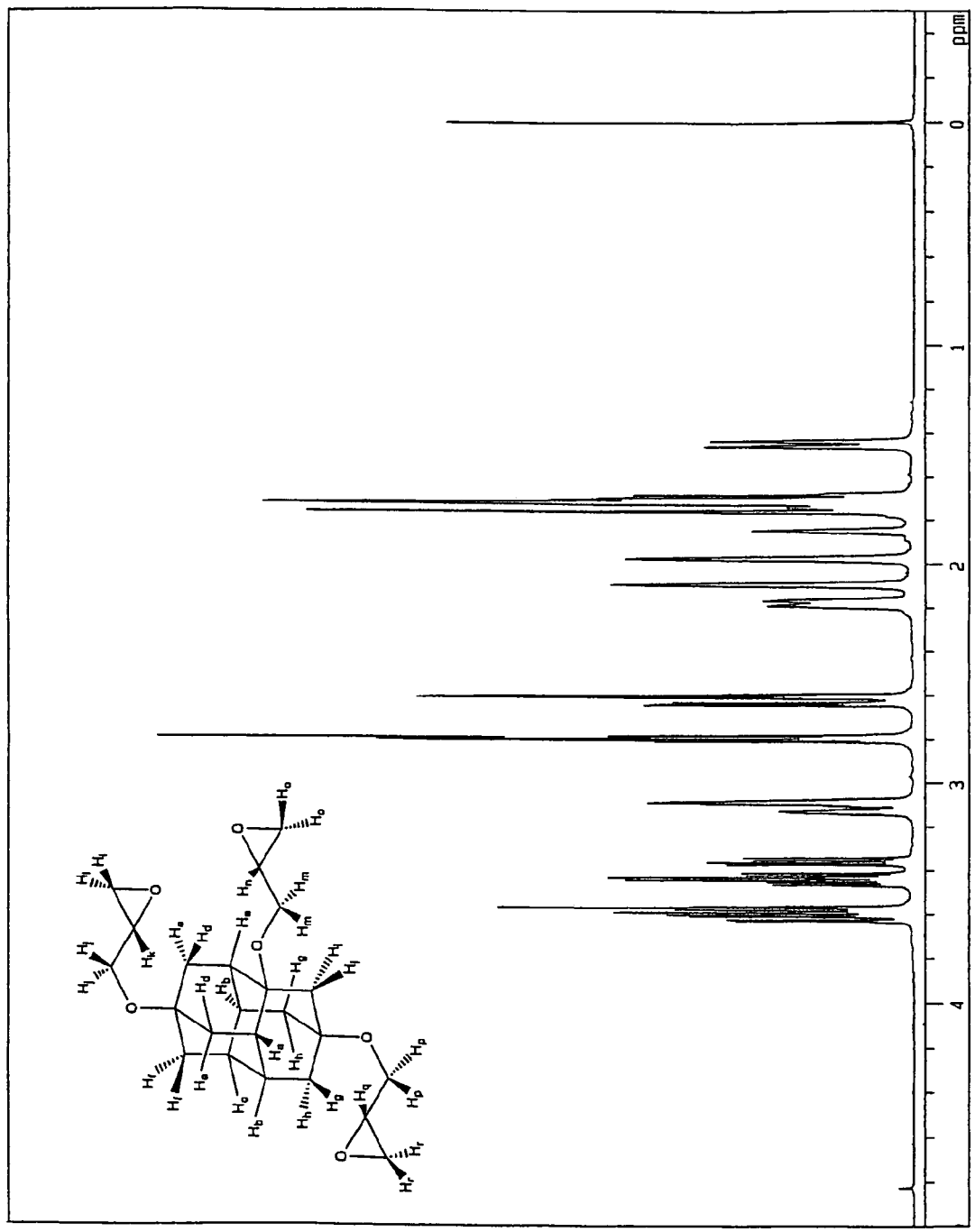
FIG. 3 shows $^1$H-NMR spectra of a 1,4,9-tris(glycidyloxy)diamantane obtained in Example 5.
Figure 4:
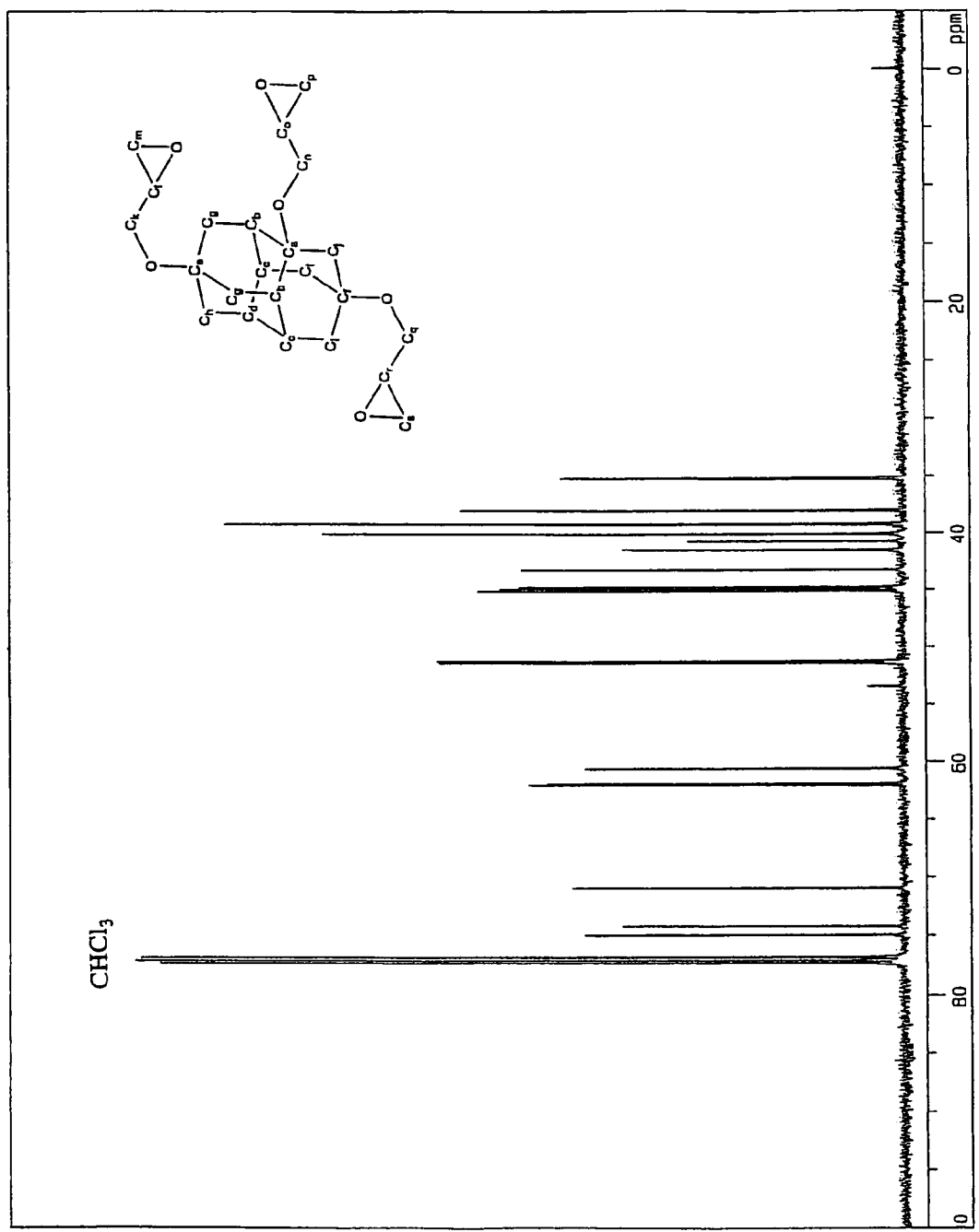
FIG. 4 shows $^{13}$C-NMR spectra of the 1,4,9-tris(glycidyloxy)diamantane obtained in Example 5.

The solid material of the by-produced m-chlorobenzoic acid was separated by filtration from the reaction solution, and the filtrate was added dropwise to 75 g of a 5% sodium sulfite aqueous solution. The methylene chloride phase was washed two times with a 1N sodium hydroxide aqueous solution in an amount of 25 g each time, and was washed four times with the ion-exchanged water in an amount of 25 g each time. The methylene chloride phase was condensed under reduced pressure to obtain 9.6 g of a transparent liquid {containing 89% of the 1,4,9-tris(glycidyloxy)diamantane}. The obtained solution was purified with a silica gel column chromatography (eluent: ethyl acetate) to obtain 7.3 g of a transparent liquid {containing 94% of the 1,4,9-tris(glycidyloxy)diamantane} in an yield of 78%. FIG. 3 shows the $^1$H-NMR spectra of the obtained compound. FIG. 4 shows the $^{13}$C-NMR spectra of the obtained compound.

MASS (EI): molecular weight (404M$^+$)

$^1$H-NMR spectra (TMS basis): δ 1.44 to 1.46 ($H_e$, d, 2H), δ 1.68 to 1.76 ($H_f$, $H_g$, $H_h$, $H_i$, m, 8H), δ 1.85 ($H_c$, s, 2H), δ 1.98 ($H_a$, s, 2H), δ 2.09 ($H_b$, s, 2H), δ 2.17 to 2.19 ($H_d$, d, 2H), δ 2.59 to 2.65 ($H_l$, $H_o$, $H_r$, m, 6H), δ 3.08 to 3.13 ($H_k$, $H_n$, $H_q$, m, 3H), δ 3.34 to 3.63 ($H_j$, $H_m$, $H_p$, m, 6H)

$^{13}$C-NMR spectra (TMS basis): δ 35.2 ($C_g$), δ 38.1 ($C_d$), δ 39.2 ($C_c$), δ 40.1, 40.7, 43.3 ($C_h$, $C_i$, $C_j$), δ 41.5 ($C_b$), δ 44.8 to 45.1 ($C_l$, $C_o$, $C_r$), δ 51.2 to 51.4 ($C_k$, $C_n$, $C_q$), δ 60.6 to 62.1 ($C_j$, $C_m$, $C_p$), δ 70.9 to 74.9 ($C_a$, $C_e$, $C_f$).

Example 6

A 4,9-diamantanediol (hereinafter abbreviated as 4,9-DAD) was used as a starting material.

Into a 200-ml four necked flask, there were introduced 4.4 g (0.02 mols) of the 4,9-DAD, 44 g of the tetrahydrofuran (in an amount 10 times as large as the 4,9-DAD on the weight basis) and 13.5 g a 3-ethyl-3-p-toluenesulfonyloxymethyloxycetane (0.05 mols, 2.5 mol times as great as the 4,9-DAD) in a nitrogen stream, which were stirred.

Next, 2.0 g (0.05 mols, 2.5 mol times of the 4,9-DAD) of 60% sodium hydride (oiliness) was washed with n-hexane, and was carefully added thereto and was stirred at a refluxing temperature for 2 hours.

Further, 8.3 g of a potassium iodide (0.05 mols, 2.5 mol times of the 4,9-DAD) was added, and was stirred at a refluxing temperature for 12 hours. Next, 44 g of the chloroform was added, and the mixture was washed 6 times with the ion-exchanged water in an amount of 44 g each time, and was condensed under reduced pressure to obtain a solid material of a cream color. The obtained solid material was purified with a silica gel column chromatography to obtain 0.38 g of a white solid material {containing 95% of the 4,9-bis[(3-ethyloxetane-3-yl)methyloxy]diamantane} in an yield of 5.1%.

Example 7

2.46 Grams (6.08 mmols) of the 1,4,9-tris(glycidyloxy) diamantane obtained in Example 5 and 1.54 g (9.16 mmols) of the 4-methylhexahydrophthalic anhydride were mixed together to obtain a total of 4.0 g of a monomer mixture. To the monomer mixture was mixed 0.02 g of a tetra-n-butylphosphonium-o,o-diethylphosphorodithioate (0.5% by weight with respect to the monomer mixture) as a cationic polymerization promoter to obtain a monomer composition. The above composition was mixed at room temperature for 30 minutes and was degassed for 10 minutes by using a vacuum pump. Thereafter, the heat-curing was effected at 100° C. for 2 hours, at 120° C. for 0.5 hours, at 150° C. for one hour and at 170° C. for one hour to obtain a transparent plate-like resin having a thickness of 1 mm.

Comparative Example 1

2.71 Grams (7.69 mmols) of a hydrogenated bisphenol A glycidyl ether (Epicoat YX8000, manufactured by Japan Epoxy Resin Co.) and 1.29 g (7.67 mmols) of the 4-methylhexahydrophthalic anhydride were mixed together to obtain a total of 4.0 g of a monomer mixture. To the monomer mixture was mixed 0.02 g of the tetra-n-butylphosphonium-o,o-diethylphosphorodithioate (0.5% by weight with respect to the monomer mixture) as a cationic polymerization promoter to obtain a monomer composition. The above composition was mixed at room temperature for 30 minutes and was degassed for 10 minutes by using a vacuum pump. Thereafter, the heat-curing was effected at 100° C. for 2 hours, at 120° C. for 0.5 hours, at 150° C. for one hour and at 170° C. for one hour to obtain a transparent plate-like resin having a thickness of 1 mm.

Comparative Example 2

2.33 Grams (6.61 mmols) of a 1,3,5-tris(glycidyloxy)adamantane and 1.67 g (9.93 mmols) of the 4-methylhexahydrophthalic anhydride were mixed together to obtain a total of 4.0 g of a monomer mixture. To the monomer mixture was mixed 0.02 g of the tetra-n-butylphosphonium-o,o-diethylphosphorodithioate (0.5% by weight with respect to the monomer mixture) as a cationic polymerization promoter to obtain a monomer composition. The above composition was mixed at room temperature for 30 minutes and was degassed for 10 minutes by using a vacuum pump. Thereafter, the heat-curing was effected at 100° C. for 2 hours, at 120° C. for 0.5 hours, at 150° C. for one hour and at 170° C. for one hour to obtain a transparent plate-like resin having a thickness of 1 mm.

Example 8

Resins of a thickness of 1 mm obtained in Example 7 and in Comparative Examples 1 and 2 were tested for their heat resistance (resistance against becoming yellow by heating) by leaving them to stand at 150° C. The degree of yellowness was evaluated by measuring the transmission factor at 400 nm. The results were as shown in Table 3.

The higher the transmission, the higher the transparency proving an excellent resistance against becoming yellow by heating (small degree of yellowness).

From the results of Table 3, it was learned that the resin obtained in Example 7 became less yellow due to the heat than the resins obtained in Comparative Examples 1 and 2.

TABLE 3

|  | 0 hr | 24 hr | 48 hr | 96 hr | 144 hr |
| --- | --- | --- | --- | --- | --- |
| Ex. 7 | 83% | 67% | 65% | 60% | 55% |
| Comp. Ex. 1 | 80% | 45% | 32% | 28% | 16% |
| Comp. Ex. 2 | 78% | 65% | 65% | 52% | 34% |

The invention claimed is:

1. A curable diamantane compound represented by the following formula (1),

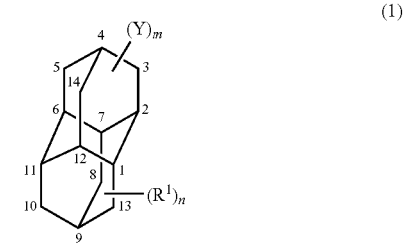

wherein m is an integer of 1 to 4, n is an integer of 0 to 4, $R^1$ is an alkyl group having 1 to 5 carbon atoms, and Y is a group represented by the following formula (2),

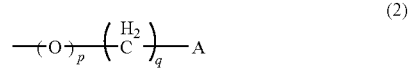

wherein p is 0 or 1, q is an integer of 0 to 6, and A is a group represented by the following formula 3(a) or 3(b),

wherein $R^2$ is a hydrogen atom, a methyl group or an ethyl group, and $R^3$ is a methyl group or an ethyl group.

2. A curable diamantane compound according to claim 1, the curable diamantane compound being represented by the following formula (4),

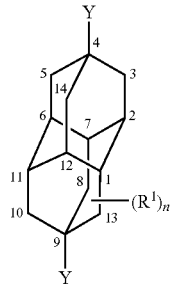

(4)

wherein $R^1$, n and Y are as defined in the above formula (1).

3. A curable diamantane compound according to claim 1, the curable diamantane compound being represented by the following formula (5),

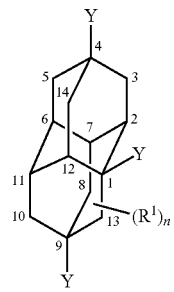

(5)

wherein $R^1$, n and Y are as defined in the above formula (1).

4. A encapsulant for a light-emitting diode comprising a curable compound of claim 1.

* * * * *